United States Patent [19]

Fanning et al.

[11] Patent Number: 5,858,792
[45] Date of Patent: Jan. 12, 1999

[54] METHOD FOR MEASURING NITRITE AND NITRATE IN AQUEOUS MEDIUM

[75] Inventors: Kent Fanning, St. Petersburg; Robert Masserini, Jr., Gulfport, both of Fla.

[73] Assignee: University of South Florida, Tampa, Fla.

[21] Appl. No.: 915,704

[22] Filed: Aug. 21, 1997

Related U.S. Application Data

[60] Provisional application No. 60/024,407 Aug. 22, 1996.
[51] Int. Cl.$^6$ ................................................. G01N 21/64
[52] U.S. Cl. .............................. 436/52; 436/110; 436/172
[58] Field of Search ............................. 436/52, 107, 110, 436/172, 174

[56] References Cited

U.S. PATENT DOCUMENTS

4,412,006  10/1983  Cox et al. ................................ 436/110
4,798,788   1/1989  Sands ........................................ 435/37

OTHER PUBLICATIONS

Lagercrantz, c., "EPR stucy of the arylnitroa anion radicals formed in the reaction between som aminoarenes, sodium nitrite and ascorbate" Chemical Abstracts, vol. 123, No. 17 (Oct. 1995), abstract No. 227474q.
Renner, G. et al "Photometric method for the determination of nitrite in aqueous solutions and in blood" Chemical Abstracts, vol. 94, No. 19 (May 1981), abstract No. 152894y.
Motomizu, S. et al, Analyst, vol. 112 (Sep. 1987) pp. 1261–1263.
"On the Optimum Conditions for the reduction of Nitrate to Nitrite by Cadmiun," Folke Nydahl, Pergamon Press, vol. 23, 1976, pp. 349–357.
"Nitrate Reductor Efficiency as an Error Source in Seawater Analysis," C. Garside, Marine Chemistry, 44, 1993, pp. 25–30.
"Automation of Flow Injection Gas Diffusion—Ion Chromatography for the Nanomolar Determination of Methylamines and Ammonia in Seawater and Atmospheric Samples," Stuart W. Gibb, John W. Wood, R. Fauzi, and C. Mantour, Journal of Automatic Chemistry, vol. 17, No. 6,, Nov.–Dec. 1995, pp. 205–212.
"An Improved Fluorescence Method for the Determination of Nanomolar Concentrations of Ammonium in Natural Waters," Ronald D. Jones, Limnol. Oceanogr., 36(4), 1991, pp. 814–819.
"Continuous Flow Fluorometric Determination of Ammonia in Water," Aoki Toyoaki, Satoshi Uemura, Mokoto Munemori, Anal. Chem., 55, 1983, pp. 1620–1622.
"Membrane Separation in Flow Injection Analysis," W.E. Van Der Linden, Analytica Chimica Acta, 151, 1983, pp. 359–369.
"Nanogram Nitrite and Nitrate Determination in Environmental and Biological Materials by Vanadium (III) reduction with Chemiluminescence Detection," Robert S. Braman and Steven A Hendrix, Anal. Chem., 61, 1989, pp. 2715–2718.

"Systematic Absorbance Errors With Technicon Autoanalyzer II Colorimeters," Philip N. Forelich and Michael E. Q. Pilson, Water Research, vol. 12, 1978, pp. 599–603.
"A Chemiluminescent Technique for the Determination of Nanomolar Concentrations of Nitrate and Nitrite in Seawater," C. Garside, Marine Chemistry, 11, 1982, pp. 159–167.
"Determination of Subnanomolar Concentrations of Nitrite in Natural Waters," Robert J. Kieber and Pamela J. Seaton, Anal. Chem., 67, 1995, pp. 3261–3264.
"Fluorometric Determination of Sub–Nanogram Levels of Nitrite Using 5–Aminofluorescein," Herman D. Axelrod and Nancy A. Engel, Analytical Chemistry, vol. 47, No. 6, May 1975, pp. 922–924.
"Determination of Nutrient Salts by Automatic Methods Both in Seawater and Brackish Water: the Phosphate Blank," X. A. Alvarez–Salgado, F. Fraga and F. F. Pérez, Elsevier Science Publishers B.V., 1992, pp. 311–319.
"Fluorometric Determination of Nitrite in Natural Waters with 3–Aminonaphthalene–1,5–Disulphonic Acid By Flow Injection Analysis," Shoji Motomizu, Hiroshi Mikasa and Kyoji Tôei, Talania, vol. 33, No. 9, 1986, pp. 729–732.
"A Submersible Flow–injection Analyser for the In–situ Determination of Nitrite and Nitrate in Coastal Waters," Anne Daniel, Dominique Birot, Stéphane Blain, Paul Tréguer, Bernard Leïldé and Eric Menut, Marine Chemisty, 51, 1995, pp. 67–77.
"Flow Injection Analysis A Practical Guide," Bo Karlberg and Gil E. Pacey, Techniques and Instrumentation in Analytical Chemistry, vol. 19, 1989, pp. 60–61.

(List continued on next page.)

Primary Examiner—Jeffrey Snay
Attorney, Agent, or Firm—Allen, Dyer, Doppelt, Milbrath & Gilchrist, P.A.

[57] ABSTRACT

A method is provided for measuring the concentration of nutrients such as nitrite and nitrate in aqueous media, e.g. the upper layers of the ocean where the concentrations of such nutrients are relatively low (i.e. in the tens of nanomoles per liter or less). The method is believed to be capable of such measurement capabilities at near real time sampling rates. The measurement of nitrite includes (a) treating an aliquot of the aqueous medium with a reagent that acidifies the aliquot, converts nitrite in the aliquot to nitrosium ion, and reacts with the nitrosium ion to yield a chemical species which fluoresces and (b) fluorometrically analyzing the resulting aliquot/reagent mixture to determine the concentration of such chemical species in the mixture, and thus to determine the concentration of nitrite in the aliquot and the aqueous medium from whence it came. The reagent is preferably an acidified solution in which the active ingredient is aniline. The measurement of nitrate is accomplished by treating a first aliquot of the aqueous medium in the manner described above to determine its nitrate concentration, treating a second aliquot (e.g. either sequentially with, or in parallel with the treatment of the first aliquot) to reduce the nitrate in the second aliquot to nitrite and measuring the resulting nitrite in the modified second aliquot in the manner described above, and using those two measurements to determine the concentration of nitrate in the second aliquot by difference.

8 Claims, 6 Drawing Sheets

OTHER PUBLICATIONS

"Simultaneou Spectrophotometric Determination of Nitrite and Nitrate by Flow Injection Analysis," Leif Anderson, *Analytica Chimic Acta*, 110, 1979, pp. 123–128.

"On–Site Automated FI Monitors Provide Near–Continuous, Reliable, and Low–Cost Data for Assessing Water Quality," Kevin N. Andrew, Nicholas J. Blundell, David Price and Paul J. Worsfold, *Analytical Chemistry*, vol. 66, No. 18, Sep. 1994, pp. 917A–922A.

"Flow Injection/Analysis," D. Betteridge, *Analytical Chemistry*, vol. 50, No. 9, Aug. 1978, pp. 832A–845A.

"A Submersible Flow Analysis System," Kenneth S. Johnson, Carl L. Beehler and Carole M. Sakamoto–Arnold, *Analytica Chimica Acta*, 179, 1986, pp. 245–257.

Continuous Determination of Nitrite Concentrations In Situ, Kenneth S. Johnson, Carole M. Sakamoto–Arnold and Carl L. Beehler, *Deep–Sea Research*, vol. 36, No. 9, 1989, pp. 1407–1413.

"Determination of Nitrate and Nintrite in Seawater by Flow Injection Analysis," Kenneth S. Johnson and Robert L. Petty, *Limnol. Oceanogr.*, 28(6), 1983, pp. 1266–1268.

"Submersible, Osmotically Pumped Analyzers for Continuous Determination of Nitrate in Situ," Hans W. Jannasch, Kenneth J. Johnson, and Carole M. Sakomoto, *Anal. Chem.*, 66, 1994, pp. 3352–3361.

"Rapid, Small–Volume, Flow Injection Analysis for $\Sigma CO_2$ and $NH_4$ in Marine and Freshwaters," Per O.J. Hall and Robert C. Aller, *Limnol. Oceanogr.*, 37(5), 1113–1119.

"Flow Injection Analysis," J. Růžiča and E. H. Hansen, *Analytica Chemica Acta*, 99, 1978, pp. 37–76.

FIG. 1.

(NOTE: WITH VALVES, ONE POSITION REPRESENTED BY ARROWS ON FULL LINES, OTHER POSITION REPRESENTED BY ARROWS ON DASHED LINES)

ANALYSIS PARAMETERS

| | | | |
|---|---|---|---|
| RUN TIME | =75.0 MIN | SAMPLE RATE | =0.5 PER SEC. |
| AMOUNT INJ. | =1.000 | DILUTION FACTOR | =1.000 |
| SAMPLE WEIGHT | =1.000 | INT STD AMOUNT | =1.000 |

STARTING PEAK WIDTH=1.0 MIN. PEAK THRESHOLD=5 AREA REJECT=100

| PK# | REF.TIME | NAME | AMOUNT | AMOUNT% | AREA | AREA% | TYPE | WIDTH | HEIGHT | HEIGHT% |
|---|---|---|---|---|---|---|---|---|---|---|
| 1 | 2.498 | | 0.0000 | 0.000 | 5346054.0 | 4.266 | BB | 0.899 | 99149.23 | 4.322 |
| 2 | 5.621 | | 0.0000 | 0.000 | 3272034.0 | 2.611 | BB | 0.916 | 59549.38 | 2.596 |
| 3 | 8.689 | | 0.0000 | 0.000 | 2999372.0 | 2.393 | BB | 0.933 | 53600.12 | 2.337 |
| 4 | 11.742 | | 0.0000 | 0.000 | 20359330.0 | 16.245 | BB | 0.893 | 380163.10 | 16.573 |
| 5 | 14.795 | | 0.0000 | 0.000 | 20755190.0 | 16.561 | BB | 0.906 | 381738.60 | 16.641 |
| 6 | 17.819 | | 0.0000 | 0.000 | 11171400.0 | 8.914 | BB | 0.898 | 207406.80 | 9.042 |
| 7 | 20.878 | | 0.0000 | 0.000 | 11244560.0 | 8.972 | BB | 0.898 | 208655.10 | 9.096 |
| 8 | 23.963 | | 0.0000 | 0.000 | 6911577.0 | 5.515 | BB | 0.936 | 123004.40 | 5.362 |
| 9 | 26.996 | | 0.0000 | 0.000 | 6365915.0 | 5.080 | BB | 0.889 | 119383.00 | 5.204 |
| 10 | 30.021 | | 0.0000 | 0.000 | 4116764..0 | 3.285 | BB | 0.947 | 72479.50 | 3.160 |
| 11 | 33.055 | | 0.0000 | 0.000 | 4029740.0 | 3.215 | BB | 0.935 | 71813.36 | 3.131 |
| 12 | 36.089 | | 0.0000 | 0.000 | 1903844.0 | 1.519 | BB | 0.907 | 34978.50 | 1.525 |
| 13 | 39.096 | | 0.0000 | 0.000 | 1936581.0 | 1.545 | BB | 0.863 | 37380.01 | 1.630 |
| 14 | 42.212 | | 0.0000 | 0.000 | 3304847.0 | 2.637 | BB | 0.963 | 57207.65 | 2.494 |
| 15 | 45.271 | | 0.0000 | 0.000 | 2511154.0 | 2.004 | BB | 0.934 | 44794.14 | 1.953 |
| 16 | 48.303 | | 0.0000 | 0.000 | 2442028.0 | 1.949 | BB | 0.962 | 42294.77 | 1.844 |
| 17 | 51.356 | | 0.0000 | 0.000 | 2168140.0 | 1.730 | BB | 0.860 | 42011.45 | 1.831 |
| 18 | 54.368 | | 0.0000 | 0.000 | 2065849.0 | 1.648 | BB | 0.924 | 37266.97 | 1.625 |
| 19 | 57.414 | | 0.0000 | 0.000 | 2992079.0 | 2.387 | BB | 0.913 | 54615.70 | 2.381 |
| 20 | 60.471 | | 0.0000 | 0.000 | 2279169.0 | 1.819 | BB | 0.900 | 42228.90 | 1.841 |
| 21 | 63.569 | | 0.0000 | 0.000 | 2578523.0 | 2.057 | BB | 0.964 | 44564.69 | 1.943 |
| 22 | 66.567 | | 0.0000 | 0.000 | 2535186.0 | 2.023 | BB | 1.012 | 41763.21 | 1.821 |
| 23 | 69.577 | | 0.0000 | 0.000 | 2033913.0 | 1.623 | BB | 0.895 | 37862.13 | 1.651 |

TOTAL AREA-125323300.0, TOTAL AMOUNT=0.0, TOTAL HEIGHT-2293913.0

METHOD FOR MEASURING NITRITE AND NITRATE IN AQUEOUS MEDIUM

GOVERNMENT SUPPORT

This invention was at least partially supported by the Office of Naval Research, under Grant Numbers N00014-94-1-0963, N00014-94-1-087, and N00014-96-1-5024.

CROSS REFERENCE TO RELATED APPLICATIONS

This application is a continuation of provisional application number 60/024,407, Method for Measuring Nitrite and Nitrate in Aqueous Solution, filed Aug. 22, 1996, now abandoned.

FIELD OF THE INVENTION

The present invention relates to the measurement of nutrients such as nitrite and nitrate in aqueous media, and particularly to the measurement of such nutrients in those parts of natural water bodies (e.g., the upper layers of the ocean) where the concentrations of such nutrients are relatively low (i.e., in the tens of nanomoles per liter or less).

INTRODUCTION/SUMMARY OF INVENTION

Nitrate and nitrite are very important nutrients to phytoplankton, the single-celled plants that are the dominant plants in the ocean, which is the largest ecosystem on Earth. Such nutrients are depleted by phytoplankton near the ocean's surface to very low levels: nanomolar or less. Yet, phytoplankton continue to grow in these regions, and chemists, utilizing techniques based on 40-year-old chemical methods, cannot detect the detailed distributions of the nutrients that are critical to phytoplankton growth. The variations in these nutrients are often a few tens of nanomoles per liter, while conventional detection limits are 200 nanomolar or higher.

According to the present invention, the measurement of nitrite in anaqueous medium comprises the steps of:

a. treating a sample of the aqueous medium with a reagent that acidifies the sample, converts nitrite in the sample to nitrosium ion, and reacts with the nitrosium ion to yield a chemical species which fluoresces, and b. fluorometrically analyzing the resulting sample/reagent mixture to determine the concentration of such chemical species in the mixture, and thus to determine the concentration of nitrite in the sample.

In the practice of the present invention, the reagent is preferably an acidified solution in which the active ingredient is aniline.

Further, according to the present invention, the measurement of nitrate in the aqueous medium comprises treating a first aliquot of the aqueous medium in the manner described above to determine its nitrite concentration, treating a second aliquot (e.g. either sequentially or in parallel with the treatment of the first aliquot) to reduce the nitrate in the second aliquot to nitrite and measuring the resulting nitrite in the modified second aliquot in the manner described above, and using those two measurements to determine the concentration of nitrate in the second aliquot by difference.

Still further, the method of the present invention contemplates different ways of reacting the nitrosium ion with reagent, depending primarily on whether there is expected to be dissolved organic matter in the sample. Where there is no or little dissolved organic matter in the sample, the flow injection method described in Example 1 can be used. However, where dissolved organic matter is present, or is expected to be present, in the sample, the reverse flow injection method, described in Example 2 is preferred. Reverse flow injection enables a baseline fluorescence value to be established from fluorescent dissolved organic matter in the sample and an additional fluorescence value to be determined for the sample due to chemical species yielded by the reaction of nitrosium ion with the reagent, thereby enabling determination of the concentration of nitrite in the sample from the difference between the baseline and additional fluorescence values.

Further features of the present invention will become apparent from the following detailed description and the accompanying drawings.

DETAILED DESCRIPTION OF THE PREFERRED EMBODIMENTS

As described, the present invention relates to a method of determining the concentrations of nitrite and nitrate in aqueous media, in a manner that is designed for near real time sampling rates, and to measure relatively low (e.g., nanomolar) concentrations of such nutrients in an aqueous medium such as seawater. The following examples describe two embodiments of the method of the present invention, utilizing flow injection techniques (Example 1) and reverse flow injection techniques (Example 2).

EXAMPLE 1 (FLOW INJECTION)

Figure 1:
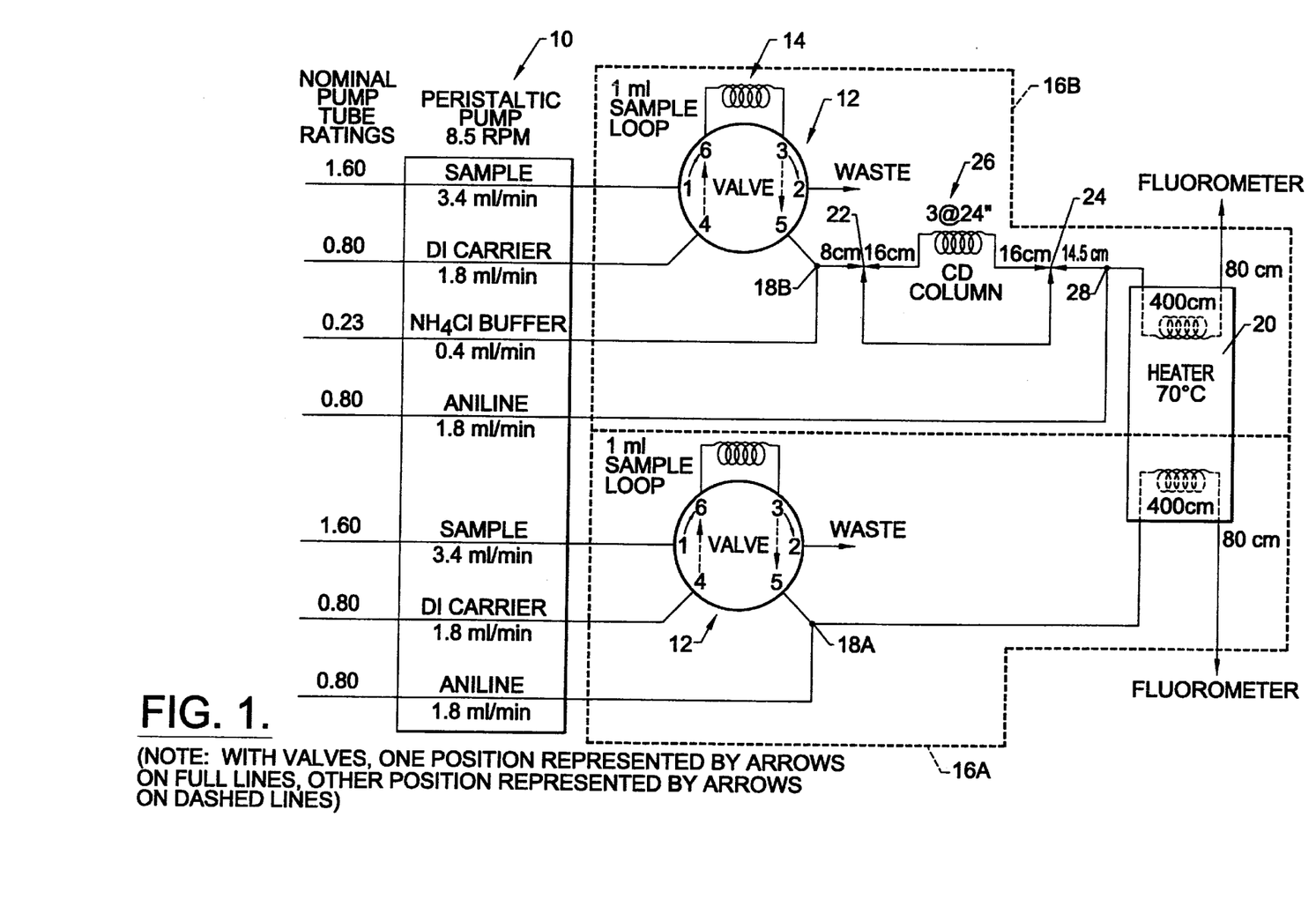
FIG. 1 is a schematic illustration of a system for use in performing a method according to one embodiment of the present invention, using flow injection techniques.
Figure 2:
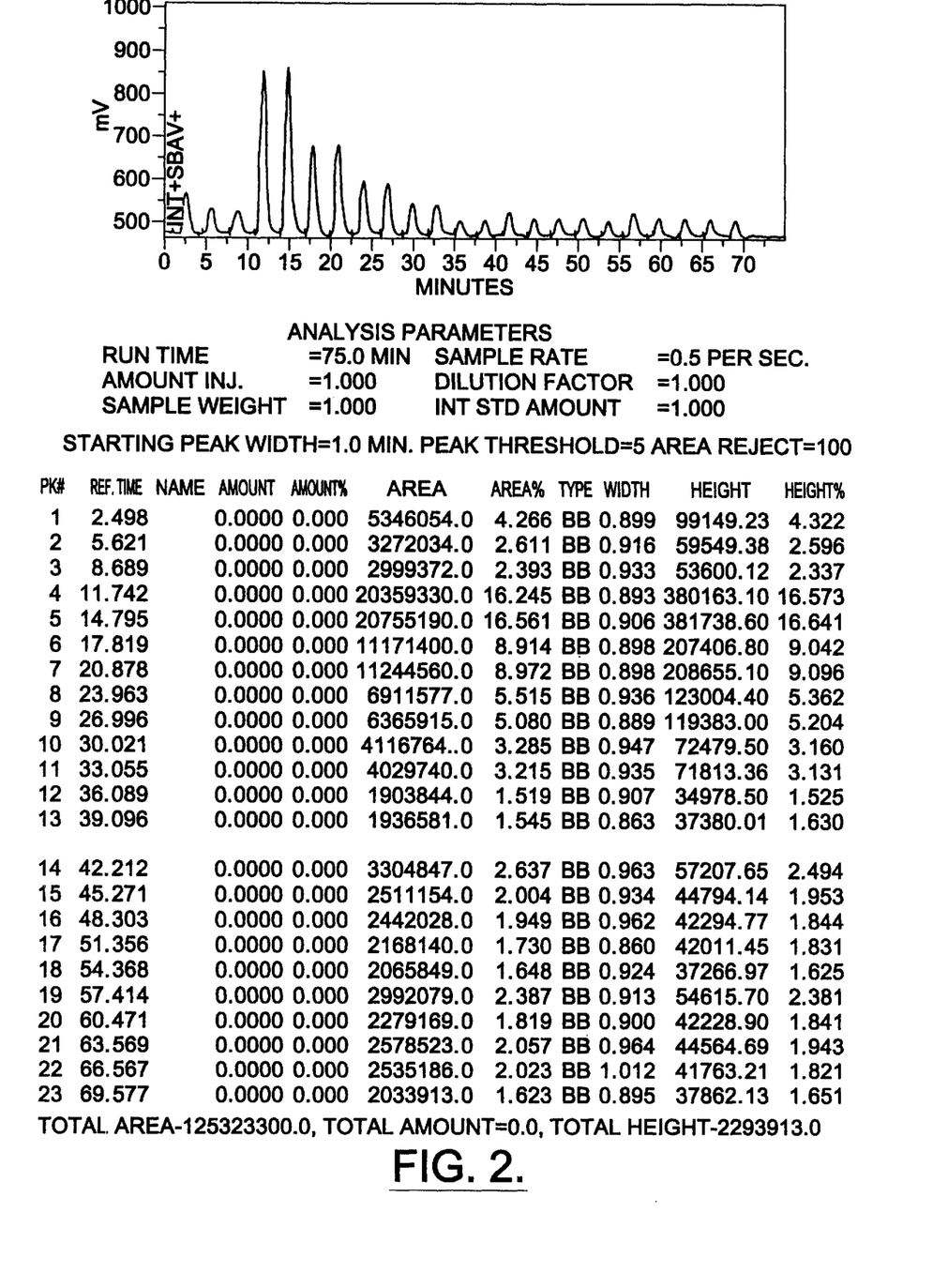
FIG. 2 illustrates fluorescent nitrite analysis of samples, prepared according to the principles of the present invention, and using flow injection techniques.
Figure 3:
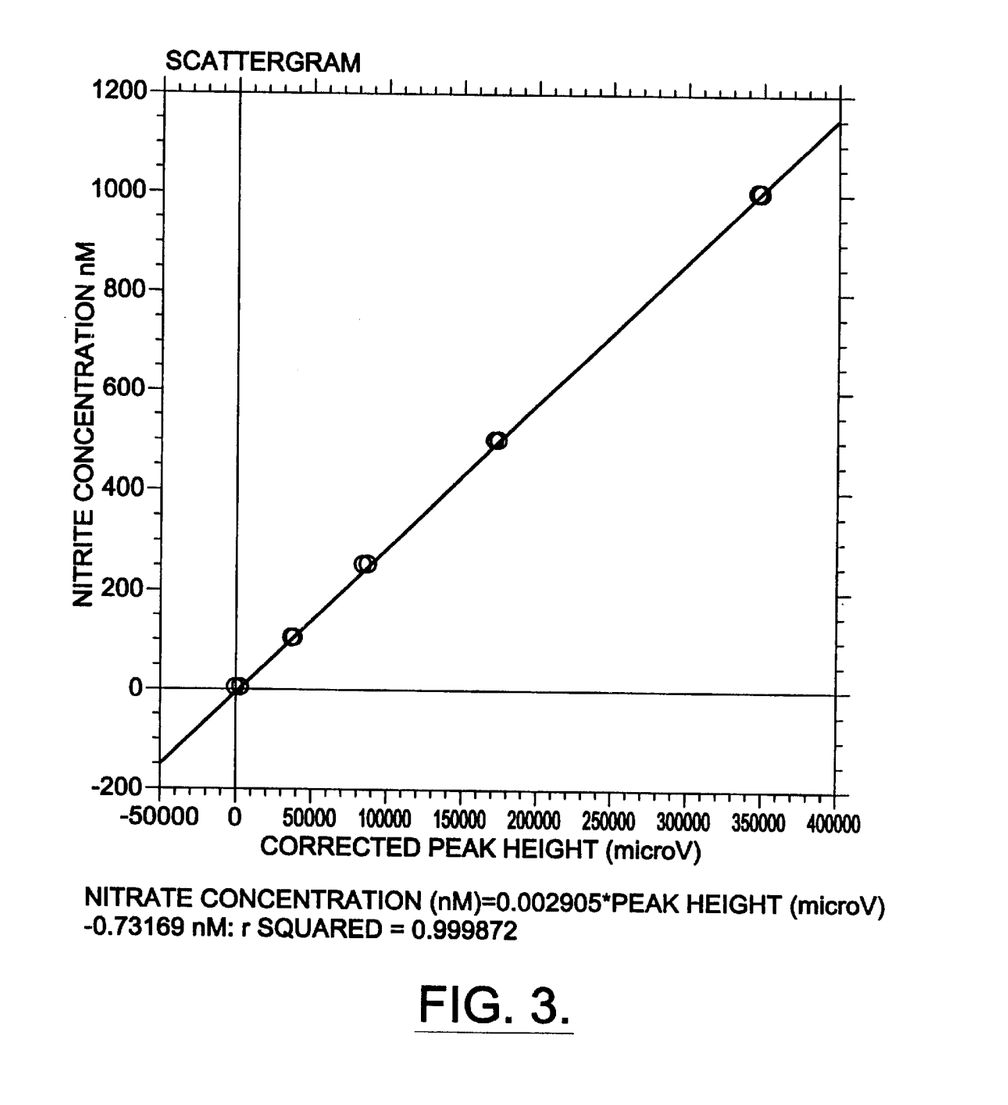
FIG. 3 illustrates data believed to validate the method of the present invention by demonstrating its linearity in the nanomolar concentration range.

The following example, illustrated in FIGS. 1–3, demonstrates the application of fluorescence-based measuring techniques involving a reaction between dissolved nitrite and an aromatic primary amine that permits intensive, detailed, and high-sensitivity surveys of both nitrite and nitrate in the upper layers of the ocean or other natural water bodies.

With the technique described in this example, which is applied utilizing an automated approach called flow-injection, nitrate and nitrite concentration down to less than 5 nanomolar can be detected while rates of sampling and analysis remain similar to those of conventional methods (e.g., about 20 determinations per hour), which is approximately the rate at which natural waters are commonly sampled down through a water column.

Theory

Nitrite can be converted to nitrosium ion by acidifying the solution. Subsequently, a diazonium ion forms via reaction of the nitrosium ion with a primary amine. An exemplary amine selected was aniline due to its simple structure, which includes a benzene ring. The product is the benzene-diazonium ion. The conjugated double bond structure of the benzene molecule contains π-bonds, which contain π-electrons that readily fluoresce. In addition, the benzene-diazonium ion contains two π-bonds in the triple bond between the two nitrogen atoms. Thus the formation of the benzene-diazonium ion from the reaction of aniline and nitrite in acidic media yields a strong change in the fluorescence due to the formation of more π-bonds.

Nitrate can be reduced quantitatively to nitrite by passing it through a copper-activated cadmium column. Once reduced to nitrite, nitrate can be analyzed utilizing the same reaction as that for nitrite. The efficiency of the reduction depends upon the flow rate through the reduction column, the bed volume of the reduction column, and the pH of the solution.

The fluorescent wavelength of excitation for any molecule can be related to its absorbance spectrum. Some of the ultraviolet and visible wavelengths at which a given molecule exhibit absorbance maxima are the wavelengths that promote electrons within a conjugated double bond structure to the $\pi^*$ state. This promotion is limited to shorter wavelengths due to the energy necessary to promote electrons between the ground and excited states in such a system. Once the wavelength of maximum absorbance of the product of the reaction of an analyte, such as nitrite, with reagent, such as aniline, has been identified, that wavelength is used as the excitation wavelength for the product ion, and the wavelength of maximum emission is then determined in the same fashion as the wavelength of maximum absorbance in absorbance spectroscopy. The emission wavelength is always longer than the excitation wavelength due to loss of energy via radiationless conversions within the molecule when the electron falls to the lowest excited state. Therefore, the preferred wavelengths for detection of the nitrite-derived benzene-diazonium ion formation are obtained in the following manner. Two spectra are determined: (1) the excitation spectrum of the 1:1 (V:V) mixture of deionized water (DIW) and 50 μL of aniline dissolved in 1 μL 10% HCl, which provides the background absorbance spectrum and (2) the excitation spectrum resulting from the reaction of a 1:1 (V:V) mixture of 1000 nM nitrite in DIW and 50 μL of aniline dissolved in 1 L 10% HCl. The difference between these two spectra yields the absorbance spectrum of the reaction. The wavelength of maximum absorbance is then used for the excitation wavelength and the fluorescent emission spectra of the two different solutions are scanned and subtracted. These experiments yield the optimal wavelengths for this fluorescence based chemistry as defined below.

Reagents are degassed for two reasons. Due to the short period of time the reaction mixture is within the analytical manifold, heating is required to increase the yield of the reaction. This heating can create bubbles of dissolved gases that, if not removed, will interfere with the fluorescence signal. Also, degassing of the 10% HCl solution prior to the addition of aniline prevents baseline drift associated with the oxidation of aniline by oxygen dissolved in the solvent.

Reagents

The deionized (DI) water for all purposes is prepared by polishing DI water with a Millipore Milli-Q RG system. The aniline reagent is composed of 1 L of degassed 10% HCl and 50 μL of aniline (from Alfa Asear). The carrier solution is degassed polished DI water. The buffer solution for nitrate reduction consists of 85.0 grams of ammonium chloride, $NH_4Cl$ (reagent grade, Aldrich Chemical Co.) diluted to approximately 950 mL with DI water. This solution is then degassed. Following the degassing, the solution is adjusted to pH 8.5 with ammonium hydroxide and diluted to 1 L with polished DI. The solutions are degassed by bubbling helium through the solutions via polytetrafluoroethylene (PTFE) tubes inserted into the flasks for thirty minutes.

System Setup

Solution delivery is accomplished via an Ismatec sixteen-channel peristaltic pump (Cole Parmer model no. H-78001-32) operated at 25% of full speed, utilizing calibrated platinum-cured silicon autoanalysis tubing to carry the solutions. The nominal ratings for tubing inside the pump were 1.60 mL/min for the sample or standard, 0.80 mL/min for the DI carrier and aniline reagent, and 0.23 mL/min for the $NH_4Cl$ buffer. These rates correspond to flow rates of 3.40, 1.80. and 0.40 mL/min at 25% of pump speed, respectively. All other tubing downstream of the pump consisted of 0.8 mm I.D. PTFE. Two position Cheminert sample injection valves 12 with micro electric actuators (Valco Instrument Company Inc. model no. C12-3116EH) and 1 mL sample loops 14 were used to introduce samples and standards into the analytical manifolds 16A,16B of the system.

As seen in FIG. 1, the nitrite analytical manifold 16A is shown at the lower portion of the system, and the nitrate analytical manifold 16B is shown at the upper portion. In the nitrite analytical manifold 16A, 400 cm of PTFE tubing follow after the point 18A where the aniline reagent is injected. The tubing is coiled inside a Technicon heater 20 (model no. B-273-27), which is reengineered with two channels of the appropriate bore PTFE tubing, and set at 70° C. In the nitrate analytical manifold 16B, 8 cm of PTFE tubing come after the buffer injection point into the carrier stream 18B, followed by a 90 degree flowpath 3-port valve 22 (Hamilton 86728). This valve, and another valve of the same type 24 just downstream of the cadmium columns 26, are used for isolation of the cadmium columns when the instrument is not being used to analyze samples. 16 cm of PTFE tubing connect the flowpath valve 22 to three 24-inch cadmium columns 26 (Irama 165-0301-24) followed by 16 cm of PTFE tubing and the second flowpath valve 24. 14.5 cm of PTFE tubing connect that flowpath valve to the aniline reagent injection point 28. The solution then flows through 400 cm of PTFE tubing in the heater 20.

It should be noted that, in both the nitrate and nitrite analytical manifolds, the analyte/reagent stream leaving the heater enters a 5-cm section of high-density microporous PTFE tubing. The purpose of this tubing is to allow the escape of any bubbles that may form in the analyte/reagent stream while it is being heated. Then, in both manifolds, the outputs of the microporous tubing are connected to Hitachi L-7480 fluorescence detectors equipped with 12 μL flow-cells. The detectors are set up using the following parameters: excitation, 220 nm; emission, 295 nm; time constant, 8 seconds; PMT, 1.

Analytical Processing

Samples and standards are introduced into the analytical manifolds by linking an A.I. Scientific XYZ autosampler (AIM 1250) to the manifold. In order to synchronize the injections with the sample or standard selection, the contact closure relays on the autosampler are used to signal the injection valve. Concord 2.0 software provided with the autosampler controls the process. An Ascentia 950N 90 MHz Pentium laptop computer controls the instrument and collects and analyzes data simultaneously.

The analog output of the detectors is digitized with a 24 bit DT2804 A/D board, which is installed in an AST docking station linked to the Ascentia computer. The digitized signal is then analyzed via Chromperfect 2.1 chromatography software (Justice Innovations), which determines the peak heights of the injected samples in a Windows® environment (FIG. 2). The multitasking environment of Windows® is required so that the autosampler could be controlled by the separate Concord 2.0 program, while data are being collected and analyzed. The peak heights of the standards are corrected for analyte present in the solvent (Low Nutrient Seawater, also referred to as LNSW) that is used to match the matrix of the samples by subtracting the average peak height of two nonspiked LNSW samples (peaks 12 and 13 in FIG. 2) from the peaks for spiked LNSW standards (peaks 4–11 in FIG. 2). The instrument standardization involves the injection of three seawater solutions to obtain equilibrium (FIG. 2, peaks 1–3), followed by duplicates of spiked LNSW samples corresponding to the following concentrations: 1000; 500; 250; 100; 0 nM nitrite (FIG. 2, peaks 4, 5; 6, 7; 8, 9; 10, 11; and 12,13; respectively). Directly following these injections, samples are injected (FIG. 2, peaks 14–23). The peak heights for all injections are imported into a Quattro Pro spreadsheet program in which a linear regression is generated for the corrected standards (FIG. 3). The function generated by this regression is then used to calculate the nitrite concentrations present in the samples.

Similar processing can be used to determine the concentration of nitrate in the sample. By reducing nitrate to additional nitrite and determining the overall nitrite concentration, the concentration of additional nitrite (due to nitrate) is thereby determined by difference.

Additional Comments

All samples of aqueous media are drawn into acid-washed, oven-dried 27 mL headspace vials (Fisher 03-340-71 A) sealed with 20 mm PTFE/silicon septa (Supelco 2-7374) and 20 mm aluminum crimps. In order to sample these sealed vials, the autosampler was adapted to use a stainless steel 12-inch 18-gauge Luer hub needle (Kontes H 90018-0012). These adaptations include an additional set screw for the probe and an acrylic plate with precisely machined holes that hold the sample vials in place when the probe exited the sample vial. In order to maintain a consistent flow of sample through the sample loop the sealed vials must be vented. This venting ss done by machining an aluminum block with two holes corresponding to the outer diameter of the 18-gauge needle and a stainless steel 22-gauge vent needle. The vent needle is attached just below the autosampler probe via a set screw on the 18-gauge needle, while the 22-gauge needle is fastened with another set screw. All connections within the manifold are made with zero dead volume flange fittings using ¼-28 thread connectors, tefzel tees, and Luer-lock connections (for the autoanalysis tubing).

Linearity of the flow injection method of the present invention is considered by the applicants to be excellent over the concentration range from 0 to 1000 nanomolar (0-1 micromolar). FIG. 3 shows a typical standard curve and standardization that demonstrates this linearity (correlation coefficient=0.999572). A high degree of linearity is important for the minimization of analytical error.

EXAMPLE 2 (REVERSE FLOW INJECTION)

Theory

The basic theory underlying the measurement of the concentration of nitrite in an aqueous medium is the same as described in Example 1. However, this example uses reverse flow injection analysis (rFIA) methodology to enable correction for dissolved organic matter (DOM) background fluorescence in the aqueous medium.

Reverse flow injection analysis methodology (rFIA) involves the injection of a precise quantity of reagent into a sample stream, which acts as the carrier stream. All the fundamental principles of flow injection analysis apply to rFIA, namely reproducible timing, injection, and dispersion. rFIA is used to correct for the DOM background fluorescence in natural samples. Once a sample's natural fluorescence achieves a plateau, the reagent is injected to develop the fluorescent signal from the nitrite present. The initial plateau height of the sample provides the natural background fluorescence, which can be subtracted from the overall sample fluorescence as the DOM matrix blank. Deionized water (DIW) is used as the baseline into which the aniline reagent is injected in order to determine the contribution of the aniline reagent to all fluorescence signals; the height of these peaks are averaged to obtain the reagent blank.

Due to the short period of time the reaction mixture is within the analytical manifold, heating is required to increase the yield of the reaction. Since dissolved gases tend to come out of solution at higher temperature, reagents are preferably degassed to reduce the likelihood of bubble formation during heating.

Reagents

Deionized water (DIW) for all purposes was prepared by polishing tap water with a Milli-Q RG system. The aniline reagent is composed of 1 L of degassed 10% HCl and 500 $\mu$l, of aniline (Alfa Asear). The wash solution is degassed polished DIW. The buffer solution for nitrate reduction consists of 8.0 grams of imidazole (reagent-grade Aldrich Chemical Co) plus 45.0 mL of $NH_4Cl/CuSO_4$ solution diluted to 1 L with polished DIW. The $NH_4Cl/CuSO_4$ solution consists of 250 g $NH_4Cl$ in 1 L DIW plus 2.5 mL of 0.08M $CuSO_4$. Cadmium for nitrate reduction is prepared from coarse ground cadmium for reduction reactors (CB/M manufacturing) by washing the cadmium three times with each of the following solutions: acetone, DI, 10% HCl, DI, $NH_4Cl$. The cadmium is then copperized by immersion in 0.08M $CuSO_4$. The remaining solution is decanted, and the cadmium is stored in the imidazole buffer. The solutions are degassed by bubbling helium through the solutions via polytetrafluorethylene (PTFE or Teflon) tubes inserted into the flasks for thirty minutes.

System Setup

Solution delivery (FIG. 4) is accomplished with an Ismatec 16-channel peristaltic pump 40 (Cole Parmer H-78001-32) operated at 25% of full speed, utilizing calibrated platinum cured silicon autoanalysis tubing to carry the solutions. The nominal pump tube ratings were: (1) 1.60 mL/min for the autosampler-to-sample selection-valve priming tube; (2) 0.80 mL/min for the sample, standard, or DIW wash and for the 10% HCl solution; (3) 0.23 mL/min for the aniline reagent; and (4) 0.03 mL/min for the imidazole buffer. At 25% of pump speed these rates correspond to flow rates of 3.40, 1.80, 0.40 , and 0.09 mL/min, respectively. All other tubing consists of 0.8 mm I.D. PTFE. Two-position six-port Cheminert injection valves 42A, 42B with micro electric actuators (Valco Instrument Company Inc. C 12-311 6EH) and 0.15 mL sample loops 44A, 44B (no additional tubing between ports 3 and 6) are used to introduce the aniline reagent into the analytical manifolds 48A, 48B. An additional two-position six-port Cheminert valve 46 is configured as a sample stream selection valve. This allows the switching of samples without introduction of an air bubble as the sample probe shifts between sample vials (i. e., when the sample is not selected, a DIW wash is).

Figure 4:
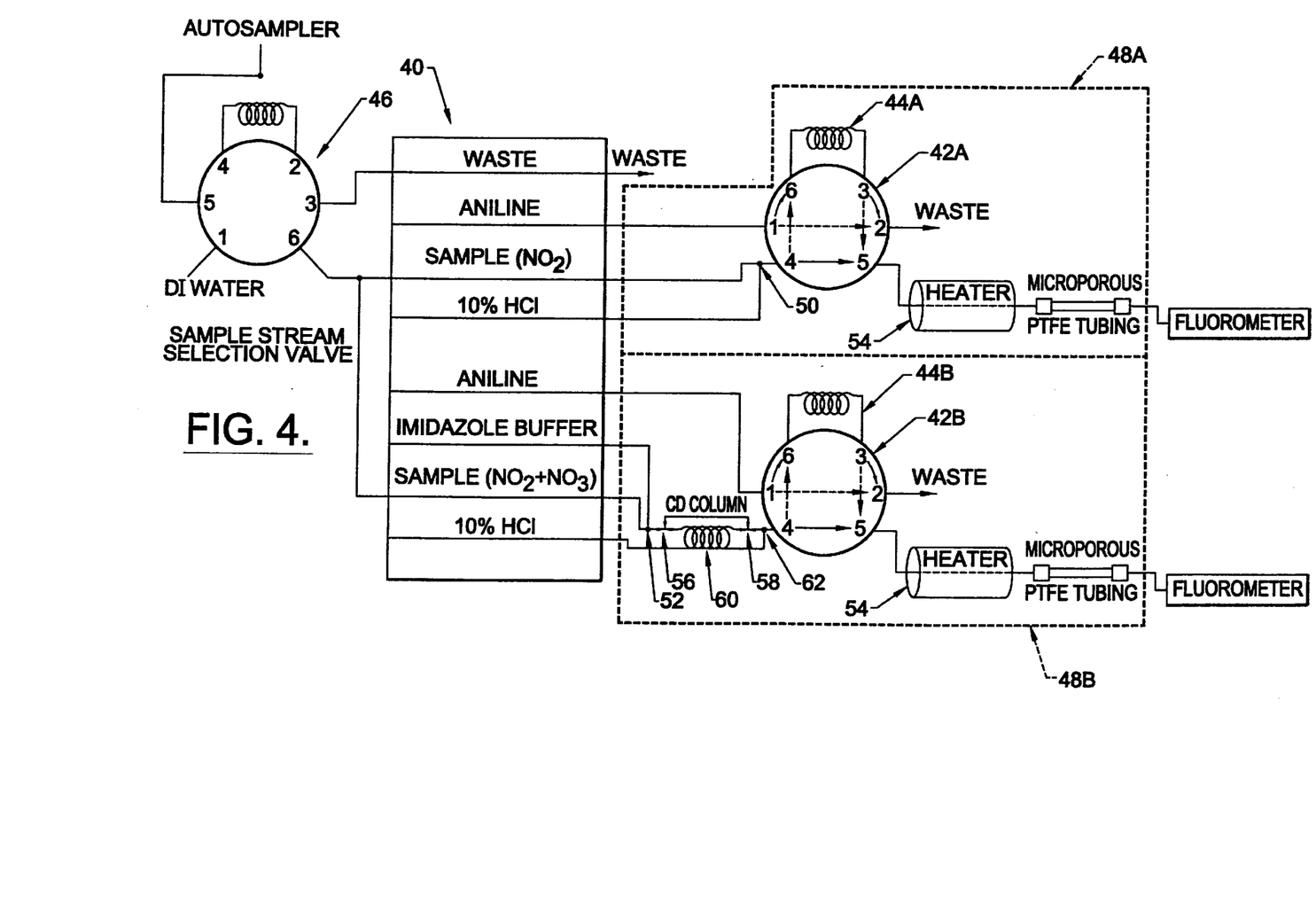
FIG. 4 is a schematic illustration of a system for use in performing a method according to another embodiment of the present invention, using reverse flow injection techniques.

The nitrite analytical manifold 48A consists of the tee 50, at which the 10% HCl reagent is injected into the sample stream connected directly to the aniline-reagent injection valve 42A. The outlet of the injection valve 42A is connected to 400 cm of PTFE tubing. This tubing is coiled inside a Technicon heater 54 (B-273-27), which is reengineered with two channels of the appropriate-bore PTFE tubing and set at 70° C. After heating, the analyte stream enters a 5-cm section of high-density microporous PTFE tubing (International Polymer Engineering); this arrangement removes any bubbles that might form as a result of the decrease in solubility of dissolved gases with the increase in temperature of the analyte stream. The nitrate analytical manifold 48B consists of 4 cm of PTFE tubing after the buffer injection point 52 into the sample stream, followed by a 90° flowpath 3-port PTFE valve 56 (Omnifit). This valve, and another valve 58 of the same type just downstream of the cadmium column 60, are used for isolation of the cadmium column when the instrument is not being used to analyze samples. The cadmium column 60 is constructed of a 13.1 cm length of hollow acrylic rod with a 1.272 cm o.d. and a 0.491 cm i.d (corresponding to a bed volume of approximately 2.2 mL) packed with coarse copperized cadmium powder (MC/B manufacturing) prepared as described above. Four cm of PTFE tubing connected the second flowpath valve 58 to the point, or tee 62, where the 10% HCl reagent is injected into the sample stream. The tee 62* where the 10% HCl was injected is connected directly to the aniline reagent injection valve 42B. The outlet of the injection valve 42B is connected to 400 cm of PTFE tubing in the heater 54. Following the heater, the sample stream flows through another 5-cm piece of high-density microporous PTFE tubing. The outlets of the microporous PTFE tubing in both manifolds are connected to Hitachi L-7480 fluorescence detectors equipped with 12 $\mu$L flowcells. The detectors are set up using the following parameters: 220 nm excitation, 295 nm emission, 8 second time constant, 1 PMT.

Samples and standards are introduced into the analytical manifolds by linking an A.I. Scientific XYZ autosampler (AIM 1250) to the manifolds. The contact closure relays on the autosampler are used to signal the injection valve actuators in order to synchronize the injections with the sample or standard selection. This is accomplished using the Concord software provided with the autosampler. At time equal to 0 seconds for a sample, the reagent injection valves 42A, 42B are set to the load position and the sample selection valve is set to the DIW wash position. At time equal to 60 seconds the sample selection valve is switched to the sample position (the 60 second period provides the wash between samples). At time equal to 195 seconds the reagent injection valves are switched to the inject position. The 135 sec period between the beginning of the sample and the injection of the reagent allows for the sample background fluorescence to achieve a plateau. Total time per sample is 200 seconds.

The analog output of the PMT detectors is digitized with a 24-bit DT2804 A/D board. The A/D board was installed in an AST docking station linked to a Ascentia 950N 90 MHz Pentium laptop computer, which controlls the instrument, collects data, and analyzes data simultaneously. Each digitized signal is then recorded and displayed in real time using Chrmperfect 2.1 for Windows® chromatography software (Justice Innovations). The multitasking environment of Windows® allows the autosampler to be controlled by a separate program, Concord 2.0, provided with the autosampler. Raw data for each analyte channel is imported into Peak Fit software 4.1. The peak heights for reagent blanks, sample background, and analyte concentration are determined via the Gaussian Deconvolution method. The parameters applied to achieve this are:

Baseline: linear/progressive, total percentage=1%;
Deconvolution: width=0.04805, standard deviation, filter=92.9;
Peak Type: spectroscopy, Voigt amplitude approximation;
Auto Scan: amplitude %=20%, vary widths, vary shape.

The autoscan peak height determinations are then exported to a spreadsheet, where all calculations were done.

To prevent initial contamination of the aqueous medium being analyzed, samples are quickly drawn into acid-washed, oven-dried, 27 mL headspace vials (Fisher 03-340-71A) sealed with 20 mm PTFE/silicon septa (Supelco 2-7374) and 20 mm aluminum crimps. In order to extract aliquots from these sealed vials, the autosampler is modified to use a stainless steel, 12 inch, 18-gauge Luer hub needle (Kontes H90018-0012). These modifications include an additional set screw for the probe and an acrylic plate with precisely machined holes that hold the sample vials in place when the probe exits the sample vial. In order to maintain a consistent flow of sample through the sample loop, the sealed vials have to be vented. This venting is done by machining an aluminum block with two holes corresponding to the outer diameter of the 18-gauge needle and a stainless steel 22-gauge vent-needle. The vent-needle assembly is attached just below the autosampler probe with a set screw on the 18-gauge needle; the 22-gauge needle is fastened with another set screw. All connections within the manifold are made with zero-dead-volume flange fittings with ¼-28 thread connectors, tefzel tees, and Luer-lock connections for the autoanalysis tubing.

Figure 5:
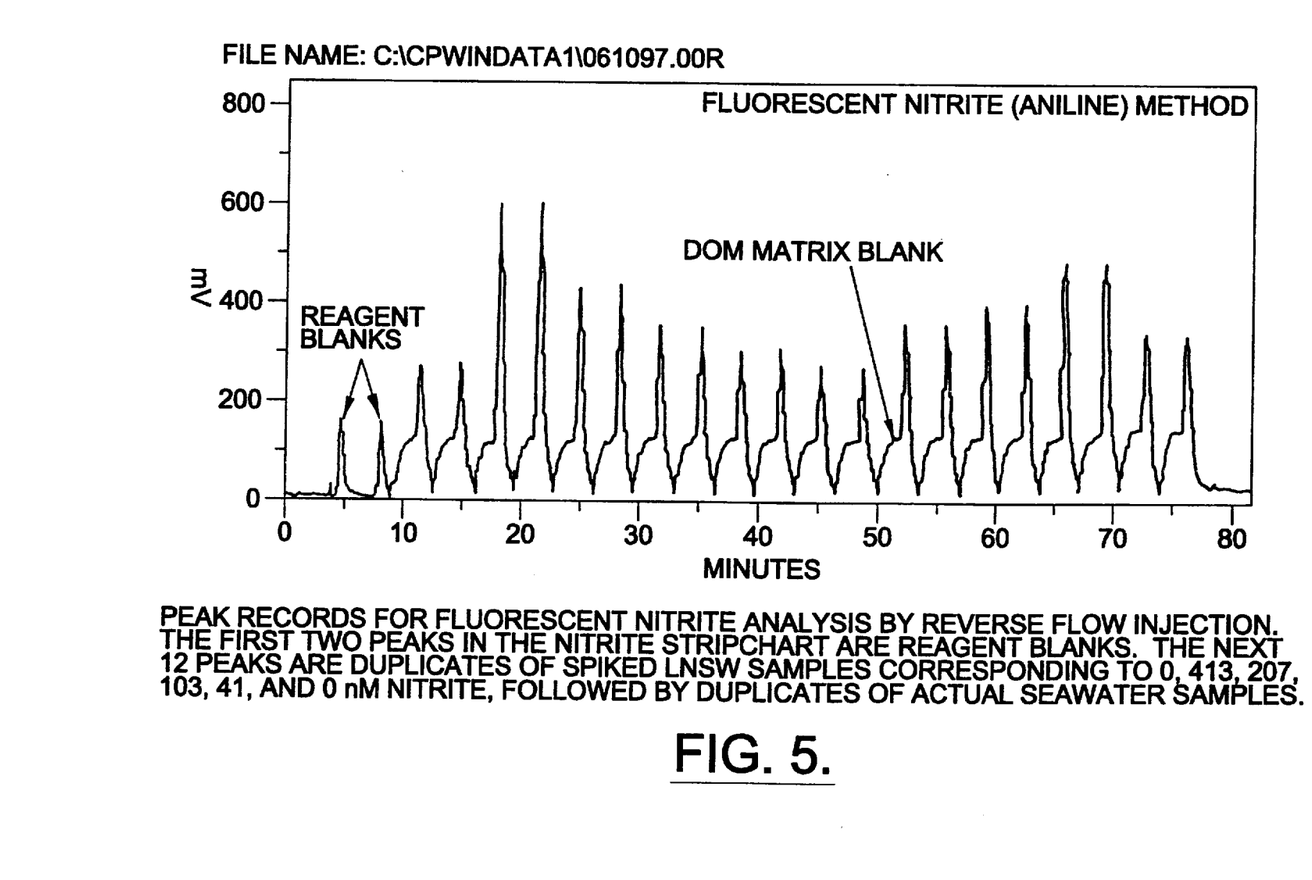
FIG. 5 illustrates fluorescent nitrite analysis of samples, prepared according to the principles of the present invention, using reverse flow injection techniques, and which samples include sea water samples with dissolved organic matter.

As seen from FIG. 5, the peak heights of the samples and standards are corrected for reagent blank fluorescence by averaging the peak heights of two reagent injections into DIW (which has no DOM). The samples and standards are also corrected for background fluorescence due to any DOM present by subtracting the plateau height of each peak prior to aniline reagent injection. The standards are then corrected for analyte present in the solvent (Low Nutrient Seawater or LNSW) used to match the matrix of the samples by subtracting the average peak height of two nonspiked LNSW samples. The instrument standardization involves the introduction of two DIW samples, followed by duplicates of spiked LNSW samples corresponding to the following concentrations: 1000, 500, 250, 100, 0 nM nitrite. Directly following the injections of these solutions, actual seawater samples are introduced into the nitrite and nitrate manifolds.

Interferences

As mentioned, it was found that dissolved organic matter (DOM) in seawater fluoresces at the wavelengths specified above. In order to correct for this false signal, rFIA is implemented. In rFIA the sample acts as the carrier, while a fixed volume of reagent is injected. This allows a background signal to be established prior to the injection of the reagent, which automatically identifies and permits the removal of the contribution of the fluorescence from DOM. Since organic leachates from tygon pump tubing positively interfere with the benzenediazonium fluorescence, platinum-cured silicon pump tubes are used to carry all solutions that enter the analytical manifold.

Additional Comments

From the results of many standardizations, the applicants believe that the linearity of the fluorescent aniline reverse-flow-injection method for nitrite in aqueous media is equivalent to the linearity of the fluorescent aniline flow-injection method for nitrite in aqueous media shown in FIG. 3.

Figure 6:
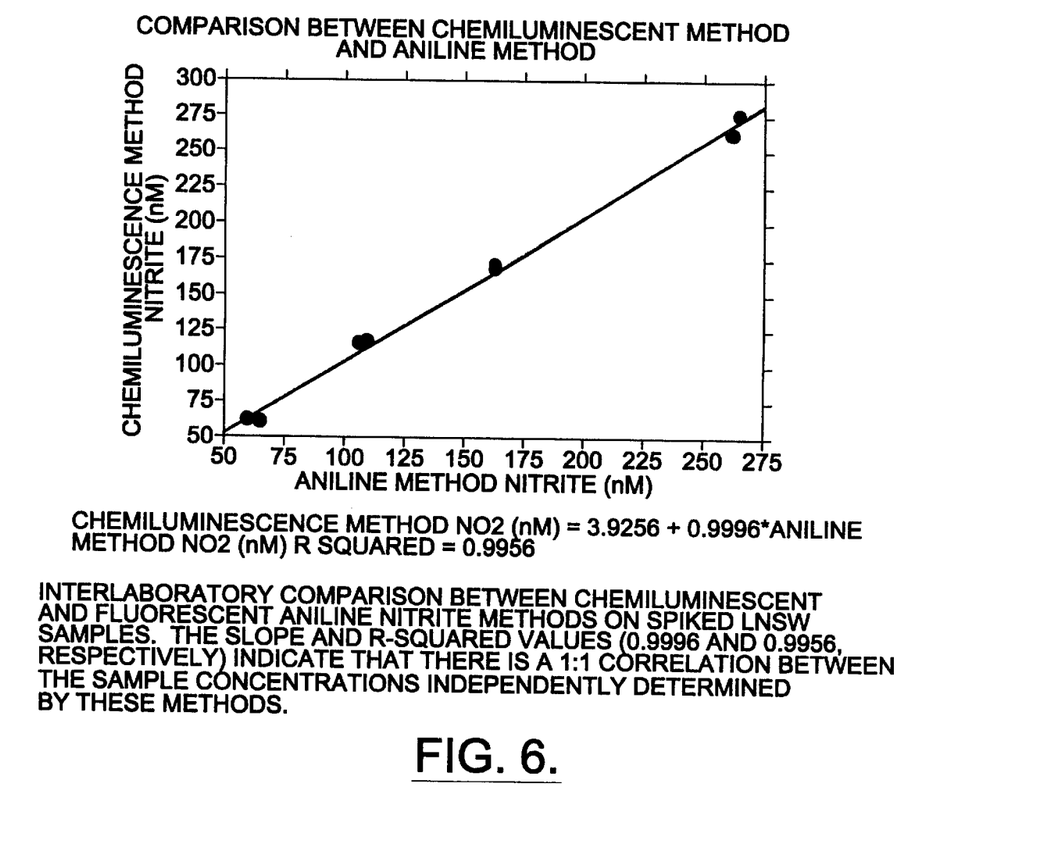
FIG. 6 presents a comparison between chemiluminescence and fluorescent aniline methods for nitrite analysis.

A well-established, albeit more cumbersome, technique for measuring nitrite (or nitrate) in aqueous media utilizes the chemiluminescence of the nitric oxide (NO) formed from nitrite (or nitrate) dissolved in such media. The applicants believe that the detection limits of the fluorescent flow-injection and reverse-flow injection technique of the present invention for nitrite (<5 nanomolar) are close to the nitrite detection limits of chemiluminescent techniques. FIG. 6 shows a comparison of nitrite concentrations in water samples measured by the fluorescent technique to nitrite concentrations in the same samples measured by a chemiluminescent technique. Note that the slope of the least-squares line through the data points is very close to unity (0.9996), that the correlation coefficient (0.9956) is also close to unity, and that the intercept of the line is approximately equal to the detection limit of the method. These features are all consistent with the claim that the two techniques are comparable.

Summary

Thus, as shown by the foregoing description, applicants have provided new and useful techniques for determining the concentration of nutrients, i.e., nitrites and nitrates in an aqueous medium such as seawater. With the foregoing disclosure in mind, it is believed the manner in which the principles of the present invention can be applied to determine the concentration of nutrients in other aqueous media will be apparent to those of skill in the art.

What is claimed is:

1. A method of measuring nitrite in an aqueous medium comprising the steps of:
   a. acidifying a sample of the aqueous medium to convert nitrite in the sample to nitrosium ion,
   b. reacting the nitrosium ion with a reagent to yield a chemical species that fluoresces, and
   c. fluorometrically analyzing the sample/reagent mixture to detect such chemical species in the mixture, and to determine the concentration of nitrite in the sample wherein the reagent is an acidified solution in which the active ingredient is aniline.

2. A method of measuring nitrate in an aqueous medium, comprising the steps of:
   a. treating a first aliquot of the aqueous medium in the manner set forth in claim 1, to determine the concentration of nitrite in the first aliquot;
   b. treating a second aliquot of the aqueous medium in a manner which reduces nitrate in the second aliquot to nitrite, producing thereby a modified second aliquot, and thereafter treating the modified second aliquot in the manner set forth in claim 1, to detect the total concentration of nitrite in the modified second aliquot, the total concentration of nitrite in the modified second aliquot being equal to the concentration of nitrite in the first aliquot plus an additional concentration of nitrite due to reduction of nitrate; and
   c. determining the concentration of nitrate in the aqueous medium by the difference in nitrite in the first and second aliquots.

3. The method as set forth in claim 1, wherein the step of reacting the nitrosium ion with a reagent comprises providing a manifold in which sample/reagent mixture is prepared for fluorometric analysis, establishing a baseline flow of a carrier into the manifold, and thereafter injecting a metered amount of sample into the carrier stream entering the manifold, the reagent being introduced into the carrier stream in a manner which enables it to mix with the sample in the carrier stream.

4. The method as set forth in claim 3, wherein the carrier comprises deionized water, and the reagent is an acidified solution in which the active ingredient is aniline.

5. The method as set forth in claim 1, wherein the step of reacting the nitrosium ion with a reagent comprises providing a manifold in which sample/reagent mixture is prepared for fluorometric analysis, establishing a baseline flow of a the sample into the manifold, and thereafter injecting a metered amount of reagent into the sample stream entering the manifold, the reagent being injected into the sample stream in a manner that enables it to mix with the sample in the stream.

6. The method as set forth in claim 5 further including the step of fluorometrically analyzing the sample/reagent mixture comprises establishing a baseline fluorescence value due to chemical species yielded by dissolved organic matter in the sample, establishing an additional fluorescence value in the sample due to chemical species yielded from the reaction of nitrosium ion with the reagent, and determining the concentration of nitrite in the sample from the difference between the baseline and additional fluorescence values.

7. The method as set forth in claim 6, wherein the reagent is an acidified solution in which the active ingredient is aniline.

8. A method as set forth in any one of claims 1–7, wherein the aqueous medium is seawater.

* * * * *